United States Patent
Binder et al.

(10) Patent No.: US 8,302,774 B2
(45) Date of Patent: Nov. 6, 2012

(54) STABILIZED GLYCERIN-IN-OIL EMULSIONS

(75) Inventors: David Alan Binder, Saddle Brook, NJ (US); Bing C. Mei, Mahwah, NJ (US); Thi N. Do, West Orange, NJ (US); George Willms, Rutherford, NJ (US); Hossein A. Baghdadi, Portland, OR (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 12/968,356

(22) Filed: Dec. 15, 2010

(65) Prior Publication Data

US 2011/0147259 A1 Jun. 23, 2011

Related U.S. Application Data

(60) Provisional application No. 61/289,047, filed on Dec. 22, 2009.

(51) Int. Cl.
*B65D 85/00* (2006.01)
*A61K 8/34* (2006.01)
*A61Q 1/06* (2006.01)
*A61P 17/18* (2006.01)
*A61P 17/00* (2006.01)

(52) U.S. Cl. .................. 206/524.1; 514/738; 424/64

(58) Field of Classification Search .................. None
See application file for complete search history.

(56) References Cited

U.S. PATENT DOCUMENTS

| 3,539,465 | A | * | 11/1970 | Hiestand et al. ........... 428/402.2 |
| 4,254,104 | A | | 3/1981 | Suzuki |
| 4,996,044 | A | | 2/1991 | Mercado et al. |
| 5,197,814 | A | * | 3/1993 | Lombardi et al. .............. 401/78 |
| 6,090,396 | A | | 7/2000 | Deckner et al. |
| 6,325,995 | B1 | | 12/2001 | El-Nokaly et al. |
| 7,115,535 | B1 | * | 10/2006 | Smith et al. ................... 442/123 |
| 7,261,877 | B2 | | 8/2007 | Luo et al. |
| 2004/0247678 | A1 | | 12/2004 | Toyoda et al. |
| 2006/0110415 | A1 | | 5/2006 | Gupta |
| 2006/0115440 | A1 | * | 6/2006 | Arata et al. ..................... 424/65 |
| 2007/0041922 | A1 | | 2/2007 | Reinhart et al. |
| 2007/0145330 | A1 | | 6/2007 | Suzuki et al. |
| 2009/0182046 | A1 | | 7/2009 | Dierker et al. |

OTHER PUBLICATIONS

Hydrogenated Castor Oil, European Phamacopoeia, 5, 2005.*

* cited by examiner

*Primary Examiner* — Robert A Wax
*Assistant Examiner* — William Craigo
(74) *Attorney, Agent, or Firm* — Joan M. McGillycuddy; Charles J. Zeller; David M. Joyal

(57) ABSTRACT

Compositions and methods are disclosed for stabilizing glycerin-in-oil emulsions, which can be used to significantly reduce thermal instability or instability over time compared to traditional cosmetics or topical formulations. The compositions comprise one or more oil-soluble rheological modifiers and optionally one or more emulsifiers in a glycerin-in-oil emulsion.

15 Claims, 4 Drawing Sheets

STABILIZED GLYCERIN-IN-OIL EMULSIONS

This application claims priority to U.S. Provisional Patent Application Ser. No. 61/289,047 filed on December 22, 2009.

FIELD OF INVENTION

The present invention relates to methods and compositions for stabilizing glycerin-in-oil emulsions. More specifically, the invention relates to stabilized cosmetic and therapeutic compositions for topical application to the outer surface and skin of the face and body, including the lips.

BACKGROUND OF THE INVENTION

Polyhydric alcohols such as glycerin have moisturizing properties when applied to the skin and lips. As such, traditional lipsticks and chapped lip products have included polyhydric alcohols such as glycerin in their formulations. Such products are typically waxy solids based on thickening agents such as ozokerite, beeswax, and candelilla wax. For example, U.S. Pat. No. 6,090,386 and U.S. Pat. No. 6,325,995 each describe lipsticks containing about 2-20% glycerin or other hydrophilic moisturizer. However, the products described therein are wax-based, and maintain a hard or durable consistency.

Glycerin-in-oil emulsions which might provide for both increased amounts of glycerin compared to wax-based products and for soft formulations for increased comfort on the lips are known to suffer from stability problems. For example, see U.S. Pat. No. 4,254,104, which describes the failure of prior art attempts to provide stable glycerin-in-oil emulsions with olive oil and surface-active agents. It is thought that the stability problems of glycerin-in-oil emulsions are due at least in part to the increased difference in density between glycerin and oil as compared to water and oil. As a result, soft formulations provided as an alternate to the traditional hard or durable lipstick fail to incorporate glycerin or other hydrophilic moisturizers. For example, see U.S. Pat. No. 4,996,044, which describes soft formulations to be applied to the lips which are free of glycerin or other hydrophilic components.

Glycerin-in-oil emulsions are particularly unstable when exposed to extremes of temperature, and in particular, at higher temperatures and oscillating temperatures involving hot and cold. These temperature extremes and changes may result in separation of phases or breaking of the emulsion. Such stability problems decrease consumer acceptance of glycerin-based products as the consumer may generally consider a product with separated phases or with leaching between phases to be unsatisfactory.

It is therefore an object of the invention to provide cosmetic and therapeutic compositions for application to the outer surface and skin of the face and body, including the lips, wherein the compositions are glycerin-in-oil emulsions with improved stability over time or improved stability when exposed to high temperatures.

SUMMARY OF THE INVENTION

In accordance with the foregoing objectives and others, the present invention provides compositions and methods for stabilizing emulsions for topical use, particularly as cosmetics for the skin, face, and lips. The emulsions are glycerin-in-oil emulsions which may optionally be anhydrous. The emulsions are stabilized to provide greater lifetime for the retail product, either at room temperature or under the temperature extremes that the retail product may encounter.

When incorporated into consumer products, emulsions according to the invention may have rheological properties to provide creamy compositions that can preferably be delivered through a hand-squeezed container or convenient cosmetic applicator. Such theological properties may include viscosity, shear dependent viscosity and/or elastic modulus (G'). In one embodiment, it has surprisingly been found that such products can be stabilized to avoid breaking or separation between the glycerin phase and the oil phase by the addition of a combination of trihydroxystearin and 12-hydroxystearic acid in an amount suitable to provide a viscosity for the emulsion at room temperature between about 2000 centipoise and about 3 million centipoise as measured by a Brookfield Viscometer (e.g. Model DV-E, Brookfield Engineering Laboratories, Inc.). In one embodiment, it has been found that products can be made with a continuous phase that exhibits an elastic modulus (G')>0 that is essentially temperature independent at temperatures between about 20° C. to about 45° C., or preferably 20° C. to about 60° C., or more preferably 20° C. to about 80° C. Thus, with increased stabilization, it is possible to formulate a variety of products in emulsion form which have improved aesthetic and functional attributes over time.

In one aspect of the invention, a glycerin-in-oil emulsion is provided. The emulsion includes (i) a continuous phase comprising one or more topically-acceptable oils, (ii) a discontinuous phase comprising glycerin as the major component, and (iii) a combination of trihydroxystearin and 12-hydroxystearic acid. When compared to an otherwise identical emulsion lacking trihydroxystearin and/or 12-hydroxystearic acid, an emulsion according to the invention has improved stability over time or when challenged at higher temperatures. Improved stability can be found in one embodiment after heating to about 49° C. for two days. Alternatively, the composition of the invention may exhibit improved stability after one week at about 49° C. In one embodiment, the stabilization challenge can occur at about 60° C. for twelve hours, or alternatively, for one week.

To achieve the desired stabilization of the glycerin-in-oil emulsion, the amount of trihydroxystearin and 12-hydroxystearic acid in combination is suitable to provide a viscosity for the emulsion at room temperature between about 2000 centipoise and about 3 million centipoise as measured by a Brookfield Viscometer (e.g. Model DV-E). In one embodiment, the rheological properties are such that the emulsion has a suitable consistency to be squeezed from a tube or similar container. In one embodiment, the trihydroxystearin is present in a range from about 0.5% to about 2.5% by weight of the emulsion, and said 12-hydroxystearic acid is present in a range from about 0.2% to about 1.5% by weight of the emulsion. Typically, the emulsion further comprises one or more emulsifiers in a total range from about 0.5% to about 6.0% by weight of the emulsion.

In one embodiment, topically-acceptable oils are present in a range from about 40% to about 90% by weight of the emulsion, glycerin is present in a range from about 5% to about 60% by weight of the emulsion, trihydroxystearin is present in a range from about 0.5% to about 2.5% by weight of the emulsion, 12-hydroxystearic acid is present in a range from about 0.2% to about 1.5% by weight of the emulsion, and one or more emulsifiers are present in a total range from about 0.5% to about 6.0% by weight of the emulsion.

Typically, the continuous phase of the emulsion according to the invention comprises one or more topically-acceptable oils and the discontinuous phase comprises glycerin as the major component. Water may be present in the emulsion, typically in the discontinuous phase. In one embodiment, the emulsion is essentially anhydrous. Emulsions according to the invention may be used in cosmetic compositions, and as such, additional components are typically present. Such components may include one or more pigments, waxes, emollients, moisturizers, preservatives, flavorants, antioxidants, botanicals, and mixtures thereof. The additional components may be present in either or both of the phases of the emulsion, or may form part of a separate phase.

The emulsion of the invention may be useful for a variety of products, including cosmetic products for the lips and face, topical products for the skin such as skin lotions and sunscreens, and therapeutic products such as hemorrhoidal creams or topical drug delivery lotions. In one embodiment, the emulsion according to the invention forms a cosmetic composition suitable for application to the lips, such as a lip moisturizer. When packaged as a consumer product such as a lip product, compositions according to the invention are typically packaged in a re-closeable container having a chamber at least partially charged with said cosmetic composition and a cap reversibly attached to said container for sealing the contents of the chamber when in a closed position and for permitting said contents to be dispensed when in an open position. Lip products according to the invention include lip cream, lip balm, lip gloss, medicated lip treatment, lip moisturizer, lip cosmetic, lip sunscreen, and lip flavorant, and the like.

These and other aspects of the present invention will become apparent to those skilled in the art according to the present description, including the claims.

DETAILED DESCRIPTION

Figure 1:
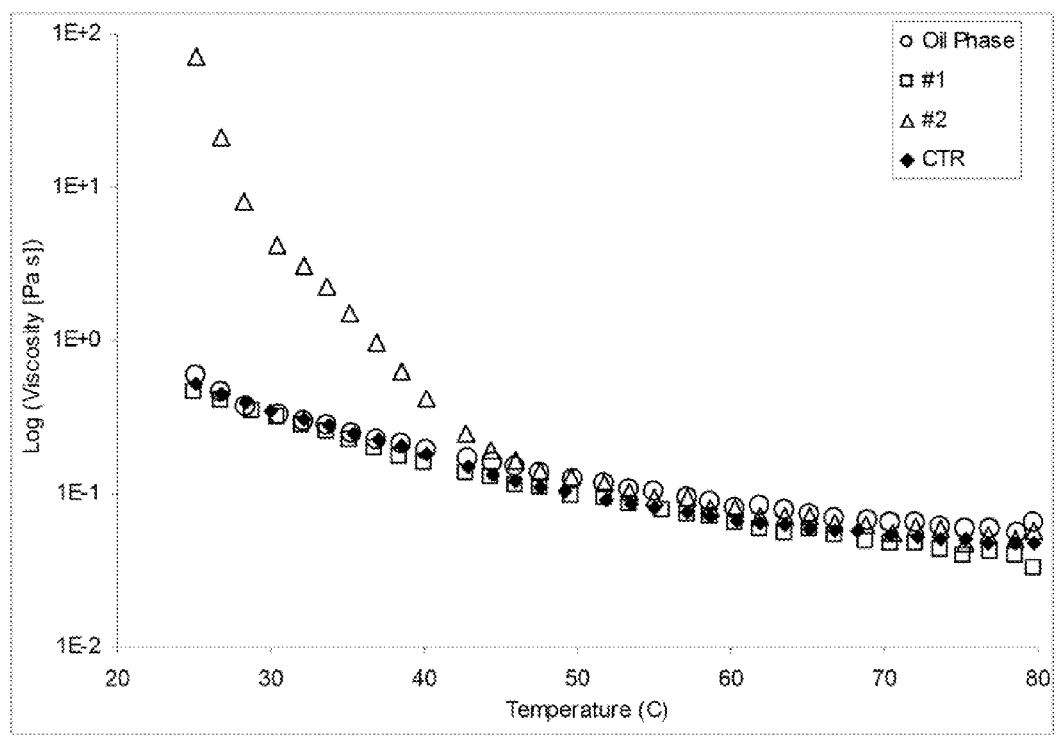
FIG. 1 shows a plot of viscosity versus temperature of various samples according to Example 4.

The present invention provides compositions and methods for stabilizing glycerin-in-oil emulsions for topical use, particularly as cosmetics for the skin, face, and lips. A stabilized glycerin-in-oil emulsion according to the invention comprises (i) a continuous phase comprising one or more topically-acceptable oils, (ii) a discontinuous phase comprising glycerin as the major component, and (iii) a combination of trihydroxystearin and 12-hydroxystearic acid in an amount suitable to provide a viscosity for the emulsion at room temperature between about 2000 centipoise and about 3 million centipoise as measured by a Brookfield Viscometer (e.g. Model DV-E). Without wishing to be bound by theory, it is thought that the specific combination of trihydroxystearin and 12-hydroxystearic acid solves the problem of providing a low enough viscosity at room temperature so that the glycerin-in-oil emulsion may be delivered in a squeeze tube or similar device while also providing physical stability for the emulsion upon exposure to higher temperatures. Alternatively, compositions according to the invention exhibit an elastic modulus (G') that is essentially temperature independent at temperatures between about 20° C. to about 45° C., or preferably 20° C. to about 60° C., or more preferably 20° C. to about 80° C.

As used herein, the stabilized emulsions of the invention have improved stability compared to an otherwise identical emulsion not containing trihydroxystearin and/or 12-hydroxystearic acid. Stability can be measured by a variety of methods according to the cosmetic arts. For example, a test of stability can be performed by heating the test composition to about 49° C. for a period of time such as overnight, one day, two days, three days, four days, five days, six days, one week, two weeks, three weeks, a month, or the like. Alternatively, a test of stability can be performed by heating the test composition to about 60° C. for one hour, six hours, twelve hours, 18 hours, one day, two days, three days, four days, five days, six days, one week, two weeks, three weeks, a month, or the like. In one embodiment, stability is tested by performing one or more freeze/thaw cycles, although glycerin-in-oil emulsions typically do not have the degree of freeze/thaw instability of water-in-oil emulsions because glycerin does not crystallize like water with a volume expansion. Evaluation of stability can be by qualitative visual inspection or may be numerically calibrated by measuring the size of separation between phases or through the growth of separation bands. In one embodiment, a stable emulsion has no visible separation. By "otherwise identical" is meant that the individual components and the amounts of components are the same with the exception of the excluded material, which can be proportionally replaced by all of the remaining components, or replaced in whole by the predominant carrier component, for example, glycerin in the discontinuous phase.

In one embodiment, a stabilized glycerin-in-oil emulsion according to the invention comprises a continuous phase comprising one or more topically-acceptable oils, a discontinuous phase comprising glycerin as the major component, and a continuous phase that exhibits an elastic modulus (G') >0 that is essentially temperature independent at temperatures between about 20° C. to about 45° C., or preferably 20° C. to about 60° C., or more preferably 20° C. to about 80° C.

Suitable non-limiting examples of oils for the continuous phase include natural and synthetic oils, including animal, vegetable, and petroleum oils; fatty acid triglycerides; fatty acid esters such as octyl palmitate, isopropyl myristate and isopropyl palmitate; ethers such as dicapryl ether; fatty alcohols such as cetyl alcohol, stearyl alcohol and behenyl alcohol; sterols; hydrocarbons such as isooctane, isododecane, isohexadecane, decane, dodecane, tetradecane, tridecane, $C_{8-20}$ isoparaffins, mineral oil, petrolatum, isoeicosane and polyisobutene; $C_{10-30}$ cholesterol/lanosterol esters; lanolin; and the like. Representative hydrocarbons include paraffinic hydrocarbons available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl R™) are also suitable. Silicone oils such as dimethicones, cyclic silicones, and polysiloxanes may also be included in the continuous phase. In one embodiment, silicone oils are present in an amount less than about 5% by weight of the continuous phase.

In a preferred embodiment, the continuous phase includes low odor lanolin. While not wishing to be bound by theory, it is thought that lanolin provides a non-water-soluble barrier when applied topically that limits the loss of transepidermal water. Other components that may provide similar benefits and that may also be suitable for the continuous phase include flax seed oil, jojoba oil, petrolatum, mineral oil, lanosterol, cholesterol esters, squalene, triglyceride oils, and low-melt waxes.

In its broadest aspects, the discontinuous phase may comprise in its major portion one or more polyhydric alcohols, such as without limitation the $C_{3-8}$ glycols, including glycerin, propylene glycol, butylene glycol, pentylene glycol, neopentyl glycol, or caprylyl glycol. Alternatively, the discontinuous phase may comprise in its major portion polyethylene glycols such as ethoxydiglycol.

In a preferred embodiment, the solvent for the discontinuous phase comprises glycerin as the major component. In one embodiment, the glycerin is USP grade glycerin. Glycerin used for the discontinuous phase may include some water. In some embodiments, the solvent for the discontinuous phase may consist essentially of glycerin, by which is meant that no additional solvents are intentionally added to the discontinuous phase, although it should be recognized that a composition consisting essentially of glycerin may contain some minor amount of water, e.g., from about 0.1% to about 4% by weight water, which may be present in cosmetic grade glycerin.

By major component is meant glycerin is present in greater than 50% by weight of the discontinuous phase. Typically, the discontinuous phase will be at least about 55% glycerin, at least about 60% by weight glycerin, at least about 65% glycerin, at least about 70% glycerin, at least about 75% glycerin, at least about 80% glycerin, at least about 85% glycerin, at least about 90% glycerin, or at least about 95% glycerin. Typically, the total amount of glycerin in the emulsion will range from about 5% to about 50% by weight of the emulsion. For example, the amount of glycerin in the emulsion may be about 10%, about 15%, about 20%, about 25%, about 30%, about 35%, about 40%, or about 45% by weight of the emulsion, or intervening values such as about 26%, about 27%, about 28%, and about 29%.

Water may be included in the discontinuous phase at less than 50% by weight of the discontinuous phase. In certain embodiments, the total amount of water in the emulsion will be less than about 20% by weight of the total emulsion, less than about 15% by weight of the total emulsion, less than about 10%, less than about 9% by weight of the total emulsion, less than about 8% by weight of the total emulsion, less than about 7% by weight of the total emulsion, less than about 6% by weight of the total emulsion, less than about 5% by weight of the total emulsion, less than about 4% by weight of the total emulsion, less than about 3% by weight of the total emulsion, less than about 2% by weight of the total emulsion, or less than about 1% by weight of the total emulsion. In some embodiments, the water content ranges from about 0.03% to about 1.2% by weight of the emulsion.

In one embodiment, the emulsion is essentially anhydrous. By essentially anhydrous is meant that water may be present only in such amounts as to have no measurable material impact on the stability of the emulsion Typically, the emulsion contains no added water, but no additional processing steps are taken to remove water from the components prior to or after addition, and no additional processing steps are taken to remove atmospheric or residual water, or to remove water that may be picked up during storage. While not wishing to be bound by theory, exclusion of appreciable amounts of water may advantageously provide additional stability over time as changes due to water evaporation over time are minimized.

Additional components providing moisturizing and/or humectant properties may be included with glycerin in the discontinuous phase. Such additional components may include propylene glycol, butylene glycol, or caprylyl glycol, or any of the glycols or polyols mentioned above.

The continuous phase will typically comprise from about 40% to about 95% of the emulsion, while the discontinuous phase will typically comprise from about 5% to about 60% of the emulsion. All ratios within the above limits are also contemplated. For example, the continuous phase may comprise about 45%, about 50%, about 55%, about 60%, about 65%, about 70%, about 75%, about 80%, about 85%, about 90%, or any other value within this range. Similarly, the discontinuous phase may comprise about 10%, about 15%, about 20%, about 25%, about 30%, about 35%, about 40%, about 45%, about 50%, about 55%, or any other value within this range.

A requirement of the emulsions according to one aspect of the invention is a combination of trihydroxystearin and 12-hydroxystearic acid. This combination will typically be present in an amount suitable to provide a viscosity for the emulsion at room temperature between about 2000 centipoise and about 3 million centipoise as measured by a Brookfield Viscometer (e.g. Model DV-E) such that the emulsion has a suitable consistency to be squeezed from a tube. Trihydroxystearin, also known as glyceryl tri(12-hydroxystearate), is the triester of glycerin and 12-hydroxystearic acid, while 12-hydroxystearic acid, also known as hydroxystearic acid or 12-hydroxy-octadecanoic acid, has the general formula:

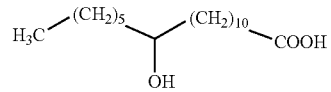

Trihydroxystearin will typically be present in a range from about 0.1% to about 2.5% by weight of the emulsion, optionally in a range from about 0.25 to about 1.0% by weight of the emulsion. For example, the amount of trihydroxystearin may be about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, or about 2.4%, or any other value to provide the required viscosity or other desired rheological property such as elastic modulus (G') in combination with hydroxystearic acid. Hydroxystearic acid will typically be present in a range from about 0.1% to about 3.0% by weight, optionally in a range from about 0.5% to about 1.5% by weight of the emulsion. For example, the amount of hydroxystearic acid may be about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.1% by weight, about 1.2% by weight, about 1.3% by weight, about 1.4% by weight, about 1.5% by weight, about 2.0% by weight, or about 2.5% by weight, or any other value to provide the required viscosity or other desired rheological property such as elastic modulus (G') in combination with trihydroxystearin.

The weight ratio of trihydroxystearin to 12-hydroxystearic acid will typically be from about 5/1 to about 1/2. Within this range, ratios of about 4/1, about 3/1, about 2/1, and about 1/1 are also contemplated to be useful.

In one embodiment, compositions according to the invention essentially exclude rheology modifiers other than trihydroxystearin and 12-hydroxystearic acid. By essentially excludes is meant that additional rheology agents are not included in such amounts that would have a measurable material impact on the viscosity of the emulsion.

By temperature independent elastic modulus (G') is meant that the average variance over the indicated temperature range from the average G' at the highest 5 degrees is less than 50%, but more typically less than 30%, or even less than 15%. For example, for the data shown in FIG. 3, the average variance was calculated by the following equation $$AvgVariance = \frac{1}{T_2 - T_1} \sum_{T_1}^{T_2} \frac{\sqrt{\left(G'_i - \frac{\sum_{T_3}^{T_2} G'_j}{T_2 - T_3}\right)^2}}{\frac{\sum_{T_3}^{T_2} G'_j}{T_2 - T_3}} \times 100$$

where G'$_i$ indicate the elastic modulus (G') at temperature x, $T_1=25°$ C., $T_2=80°$ C. and $T_3=75°$ C.

Typically, emulsions according to the invention further comprise one or more emulsifiers. For example, the one or more emulsifiers may be present in a total range from about 0.01% to about 10.0% by weight of the emulsion. In some embodiments, the total amount of emulsifier ranges from about 0.1% to about 6.0% be weight, or from about 0.5% to about 4.0% by weight. In some embodiments, the total amount of emulsifier is about 2% by weight, or about 4% by weight of the emulsion.

Emulsifiers having a lower HLB value may be suitable for use in glycerin-in-oil emulsions. For example, such emulsifiers may have a low HLB of below 10, or below 8.5. In certain embodiments, HLB values between 2 and 5 are preferred. In one embodiment, one or more low HLB emulsifiers is used in combination with a higher HLB emulsifier. Examples of emulsifiers include polyglyceryl compounds such as polyglyceryl-6-polyricinoleate, polyglyceryl pentaoleate, polyglyceryl-isostearate, and polyglyceryl-2-diisostearate; glycerol esters such as glycerol monostearate or glycerol monooleate; phospholipids and phosphate esters such as lecithin and trilaureth-4-phosphate (available under the tradename Hostaphat® KL-340-D); sorbitan-containing esters (including SPAN® esters) such as sorbitan laurate, sorbitan oleate, sorbitan stearate, or sorbitan sesquioleate; polyoxyethylene phenols such as polyoxyethylene octyl phenol; polyoxyethylene ethers such as polyoxyethylene cetyl ether and polyoxyethylene stearyl ether; polyethylene glycol emulsifiers such as PEG-30-polyhydroxystearate or alkylpolyethylene glycols; polypropylene glycol emulsifiers such as PPG-6-laureth-3; dimethicone polyols and polysiloxane emulsifiers; and the like. Combinations of emulsifiers, such as the combination of lecithin and sorbitan, are envisioned. Additional emulsifiers are provided in the INCI Ingredient Dictionary and Handbook, 12$^{th}$ Edition, 2008, the disclosure of which is hereby incorporated by reference.

In one embodiment, emulsions according to the invention may contain one or more topically-acceptable oils in the continuous phase, typically present in a range from about 40% to about 95% by weight of the emulsion, more typically from about 55% to about 75%; glycerin typically present in a range from about 5% to about 60% by weight of the emulsion, more typically from about 20% to about 40%; trihydroxystearin present in a range from about 0.1% to about 2.5% by weight of the emulsion, more typically from about 0.25% to about 1.0% by weight; and 12-hydroxystearic acid present in a range from about 0.1% to about 3.0% by weight of the emulsion, more typically from about 0.5% to about 1.5%. Typically, the emulsion will further contain one or more emulsifiers in a total range from about 0.5 to about 3.0% by weight of the emulsion.

Emulsions according to the invention are particularly suitable for cosmetic compositions for topical application. When formulated as cosmetic compositions, the emulsions will typically include additional components optionally distributed in either or both phases of the emulsion. Such components may be selected from the group consisting of pigments, waxes, emollients, moisturizers, preservatives, flavorants, antioxidants, botanicals, and mixtures thereof. Particular mention may be made of highly purified botanical extracts or synthetic agents which may have wound-healing, anti-inflammatory, or other benefits useful for treating the skin or lips. The compositions may include one or more film-formers to increase the substantivity of the product. In certain embodiments, compositions according to the invention provide high moisturization readings upon topical application due to the presence of high levels of glycerin while also achieving consumer acceptance due to increased stability.

The compositions of the invention will typically comprise less wax than customarily found in lip products. In some embodiments, less than about 10% by weight of the composition is wax. More typically, compositions contain less than about 5% by weight wax, and may even comprise less than about 1% by weight wax, or be wax free.

Additional components may be added to impart additional functionality. For example, particulate material may be added for ultraviolet (UV) light absorption or scattering, such as titanium dioxide and zinc oxide particulates, or for aesthetic characteristics, such as color (e.g., pigments), pearlescence (e.g., mica), or the like. Additional embodiments may include antioxidants such as tocopherol. Alternatively, the emulsions according to the invention may be used as the delivery vehicle for a topically-active pharmaceutical, for example, in a hemorrhoidal treatment.

In one embodiment, the emulsions according to the invention are provided as retail products for application to the lips. Accordingly, such lip products may include lip cream, lip balm, lip gloss, medicated lip treatment, lip moisturizer, lip cosmetic, lip sunscreen, and lip flavorant. In one embodiment, the lip product is a creamy, flowable lip product. In certain embodiments, products according to the invention may have the consistency of a semi-viscous liquid or paste.

When formulated as lip products, the emulsions according to the invention may be packaged in a re-closeable container. Such containers may include an enclosure or chamber charged with the emulsion formulated as a cosmetic composition and a cap removably attached to the container or reversibly configured on the container. In one embodiment, a cap may be attached to a squeezable enclosure such that the cap can be removed from the orifice of the squeezable enclosure, and replaced upon completion of dispensing of the composition. A cap may be attached to the body of a squeezable enclosure to facilitate re-sealing the squeezable enclosure for storage between uses. In one embodiment, the cap is reversibly attached to the container for sealing the contents when in a closed position and for permitting the contents of the container to be dispensed when in an open position. Various containers are envisioned, including without limitation click pens, pumps, air-less pumps, pressurized packages, hand-squeezed containers, a cosmetic applicator, and the like.

Additional components may be incorporated as fillers or for various functional purposes as is customary in the cosmetic arts. However, while additional components consistent to formulate the above cosmetic compositions may be included, the inclusion of additional ingredients is limited to those ingredients which do not interfere with the formation of a glycerin-in-oil emulsion.

EXAMPLES

Glycerin-in-oil emulsions according to the invention may be prepared according to the following general procedure. Oils and waxes (if present) are added to a batch container and heated until all components are melted, generally to about 85° C. Powders are added with milling (homogenization) individually until well dispersed, followed by addition of pigments and/or pigment grinds, and addition of other non-temperature-sensitive functional components. The glycerin phase is heated to about 85° C., and slowly added to the main batch with homogenization. The combined mixture is cooled with milling to a temperature of about 60° C., followed by addition of fragrance and temperature sensitive actives. The composition is cooled to about 55° C. with slow mixing and placed in testing equipment or packaged for evaluation. Stability may be evaluated for separation between phases and presence of banding.

Example 1

Emulsion formulations A-D were prepared according to the following table. All amounts are given in weight percent of the components.

TABLE I

| name/description | A | B | C | D |
|---|---|---|---|---|
| $C_{10\text{-}30}$ cholesterol/lanosterol esters | 27.0 | 29.0 | 28.0 | 27.5 |
| low odor lanolin | 30.0 | 30.0 | 30.0 | 30.0 |
| glycerin | 30.0 | 30.0 | 30.0 | 30.0 |
| trihydroxystearin | 1.0 | 1.0 | — | 1.0 |
| hydroxystearic acid | 0.5 | 0.5 | 0.5 | — |
| polyglyceryl-6-polyricinoleate, polyglyceryl-2-isostearate, disteardimonium hectorite, and trace antioxidant | 2.0 | — | 2.0 | 2.0 |
| sunscreen agent | 9.0 | 9.0 | 9.0 | 9.0 |
| caprylyl glycol | 0.5 | 0.5 | 0.5 | 0.5 |
| total | 100.0 | 100.0 | 100.0 | 100.0 |

Upon visual inspection for stability, formulation A showed no separation after overnight treatment in a 60° C. oven. Formulations B and C showed some separation, and D showed somewhat less separation compared to B and C under the same conditions. After one week at 60° C., formulation A continued to show no separation, formulation B exhibited no additional separation compared to the overnight result, and formulations C and D showed increased separation compared to their overnight results, respectively. The results suggest that formulations C and D would be considered unacceptable for a commercial product.

In an alternate stability test, formulation A showed no separation after two days or one week at about 49° C. (120° F.). Formulation B showed some separation at two days and with a minimal increase in separation after one week under the same conditions. Formulation C exhibited significant separation at two days and one week. Formulation D showed minor separation at two days and a significant increase in separation at one week under the same conditions. The results suggest that formulations C and D would be considered unacceptable for a commercial product.

Example 2

Emulsion formulation E was prepared according to the following table. All amounts are given in weight percent of the components.

TABLE II

| name/description | E |
|---|---|
| $C_{10\text{-}30}$ cholesterol/lanosterol esters | 25.0 |
| lanolin | 30.0 |
| glycerin | 30.0 |
| trihydroxystearin | 0.5 |
| hydroxystearic acid | 1.0 |
| polyglyceryl-6-polyricinoleate, polyglyceryl-2-isostearate, disteardimonium hectorite, and trace antioxidant | 4.0 |
| petrolatum | 9.0 |
| caprylyl glycol | 0.5 |
| total | 100.0 |

Example 3

Emulsion formulation F was prepared according to the following table. All amounts are given in weight percent of the components.

TABLE III

| name/description | F |
|---|---|
| skin conditioning agents | 7.40 |
| botanical extracts | 8.00 |
| lanolin | 30.00 |
| glycerin | 28.80 |
| trihydroxystearin | 2.00 |
| hydroxystearic acid | 1.00 |
| polyglyceryl-6-polyricinoleate, polyglyceryl-2-isostearate, disteardimonium hectorite, and trace antioxidant | 2.00 |
| preservative | 0.50 |
| film former | 5.00 |
| antioxidants | 1.20 |
| pigments and cosmetic powder | 13.50 |
| flavorant | 0.60 |
| total | 100.00 |

Emulsion F was challenged with three freeze/thaw cycles. Upon observation, no separation in the emulsion was present after the third cycle. No separation was observed for formulation F after three weeks at room temperature or one week at 49° C. (120° F.).

Example 4

An oil phase was prepared according to the following table:

TABLE IV

| name/description | |
|---|---|
| $C_{10\text{-}30}$ cholesterol/lanosterol esters | 40.91 |
| low odor lanolin | 45.45 |
| sunscreen agent | 13.64 |
| total | 100.0 |

Test compositions were prepared according to the following table:

TABLE V

| name/description | CTR | 1 | 2 | 3 | 4 | 5 |
|---|---|---|---|---|---|---|
| oil phase | 97.78 | 97.78 | 97.78 | 97.78 | 97.78 | 97.78 |
| trihydroxystearin | 1.48 | 2.22 | | | | |
| hydroxystearic acid | 0.74 | | 2.22 | | | |
| carnauba | | | | 2.22 | | |
| ozokerite | | | | | 2.22 | |
| polyethylene-linear | | | | | | 2.22 |
| total | 100 | 100 | 100 | 100 | 100 | 100 |

Method: Each sample was loaded into the rheometer (AR G2 Rheometer; TA Instruments, Inc.; Geometry: 40 mm parallel plates, with a 1 mm gap between the two plates). The sample was loaded between the two plates at 80° C. and the excess material was trimmed. After the sample was loaded, it was pre-sheared for 1 minute at a shear rate of 5 Hz. This conditioning step was performed to ensure loading reproducibility. The sample was then measured in a temperature sweep as it was cooled from 80° C. to 25° C. at a cooling rate of 5 degrees per minute. During measurement, the sample was oscillated at 1 Hz and at a controlled strain of 1%.

FIG. 1 shows a plot of viscosity versus temperature for oil phase, composition 1, composition 2, and composition CTR. FIG. 1 shows that the combination of trihydroxystearin and hydroxystearic acid (labeled CTR) is more temperature-independent compared to the oil phase combined with hydroxystearic acid alone (labeled 2).

Figure 2:
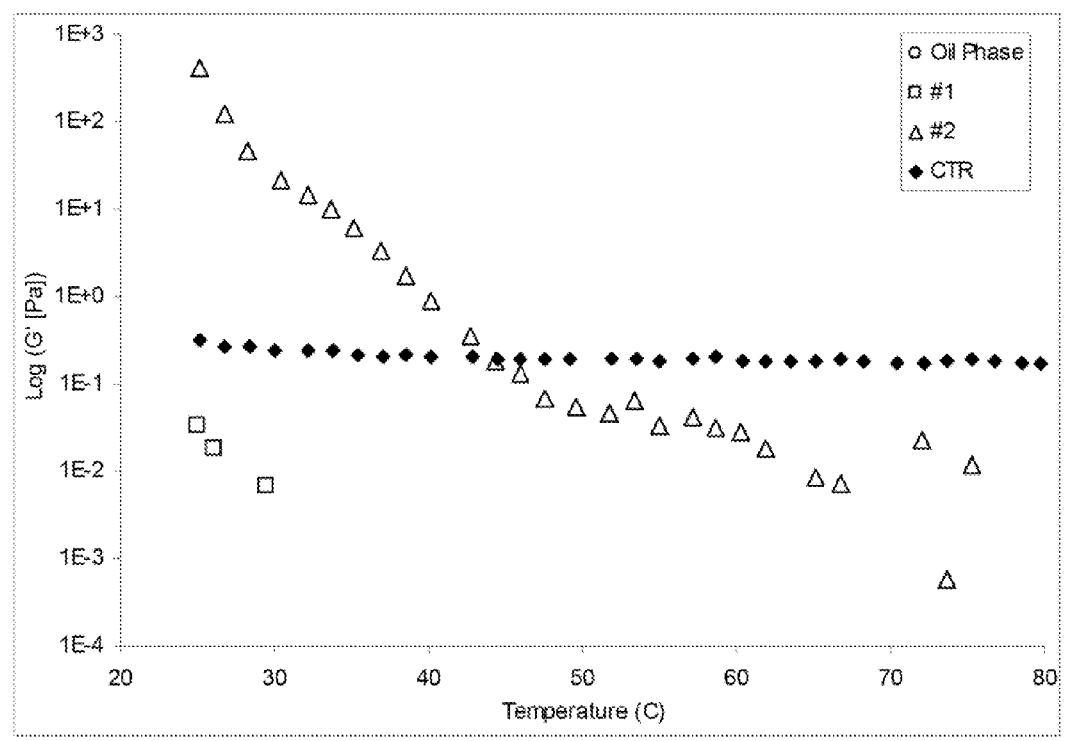
FIG. 2 shows a plot of elastic modulus (G') versus temperature for various samples according to Example 4.

FIG. 2 shows a plot of elastic modulus (G') versus temperature for oil phase, composition 1, composition 2, and composition CTR. FIG. 2 shows that the sample with both hydroxystearic acid and trihydroxystearin (labeled CTR) exhibits a beneficial effect compared to the components incorporated into the composition individually. The CTR sample exhibits an elastic modulus (G') which is relatively temperature insensitive, and higher in value at higher temperatures compared to the other formulas. Data points from the oil phase alone and the oil phase with trihydroxystearin (labeled 1) are not visible in the FIG. 2 because the figure is plotted in log scale, which does not display negative numbers.

Figure 3:
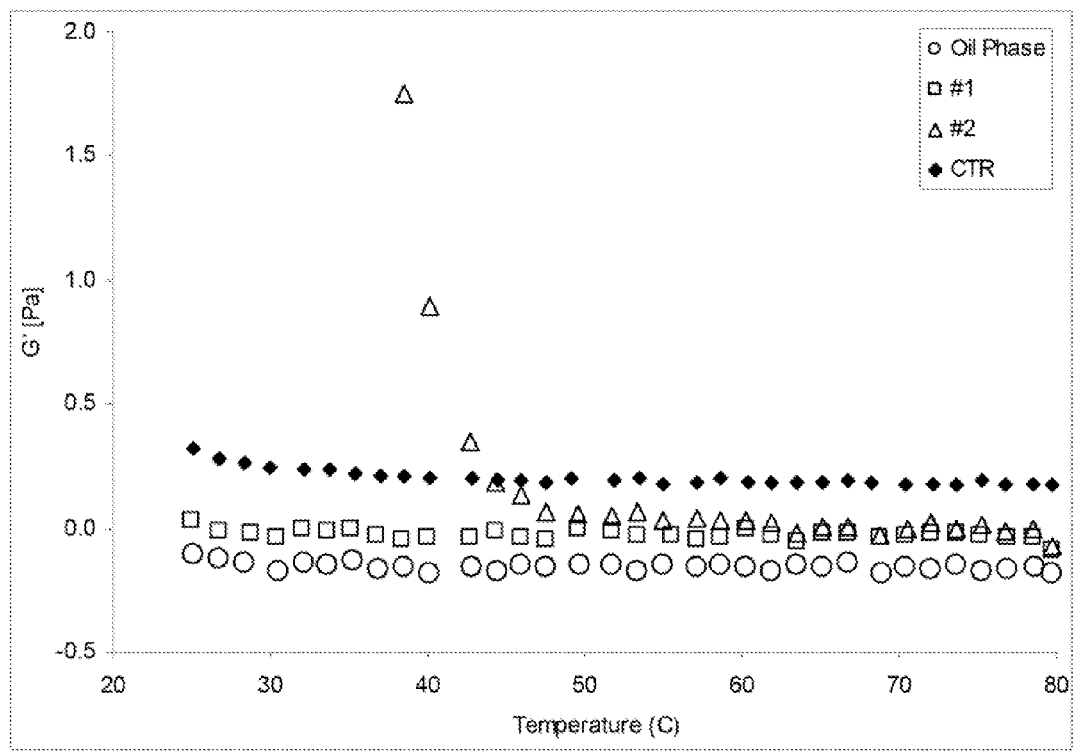
FIG. 3 shows a plot of elastic modulus (G') versus temperature of various samples in linear scale according to Example 4.

FIG. 3 shows a plot of elastic modulus (G') versus temperature for oil phase, composition 1, composition 2, and composition CTR. FIG. 3 is presented in linear scale to verify that the elastic modulus (G') of the oil phase and the oil phase with trihydroxystearin (labeled 1) were essentially zero.

Figure 4:
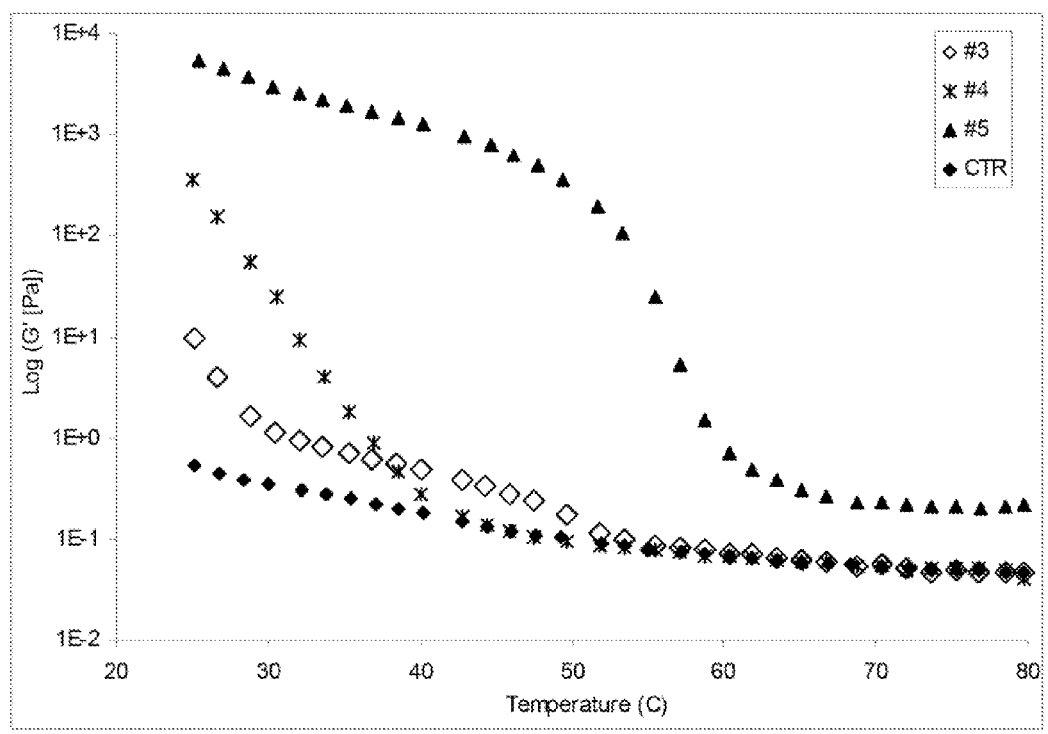
FIG. 4 shows a plot of elastic modulus (G') versus temperature with various waxes according to Example 4.

FIG. 4 shows a plot of elastic modulus (G') versus temperature with various waxes according to the compositions of TABLE V. Measurements against oil phases with waxes used as structure-providing materials do not show the behavior as demonstrated by the oil phase with trihydroxystearin and hydroxystearic acid (labeled CTR). The oil phase with trihydroxystearin and hydroxystearic acid can be seen to provide a composition that exhibited a temperature independent elastic modulus greater than 0.1 Pa. The waxes that were tested for comparison were carnauba, ozokerite and polyethylene, and these waxes did not offer the benefit as observed in an oil phase with hydroxystearic acid and trihydroxystearin combined. The oil phase having both hydroxystearic acid and trihydroxystearin in combination formed a structured viscoelastic composition that exhibited a temperature-independent elastic modulus (G'). This benefit was not observed by incorporating only one of these two components nor the common waxes according to TABLE V.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A stabilized glycerin-in-oil emulsion comprising:
   (i) a continuous phase comprising one or more topically-acceptable oils,
   (ii) a discontinuous phase comprising glycerin as the major component, and
   (iii) a combination of trihydroxystearin and 12-hydroxystearic acid in an amount suitable to provide a viscosity for the emulsion at room temperature between about 2000 centipoise and about 3 million centipoise:
   wherein a weight ratio of trihydroxystearin to 12-hydroxystearic acid is not greater than about 5/1; and
   wherein said emulsion has improved stability compared to an otherwise identical emulsion not containing trihydroxystearin and/or 12-hydroxystearic add.

2. An emulsion according to claim 1, wherein said emulsion further comprises one or more emulsifiers in a total range from about 0.5% to about 6.0% by weight.

3. An emulsion according to claim 2, wherein said trihydroxystearin is present in a range from about 0.5% to about 2.5% by weight, and said 12-hydroxystearic acid is present in a range from about 0.2% to about 1.5% by weight.

4. An emulsion according to claim 3, wherein said emulsion is stable as an emulsion after heating to about 49° C. for two days.

5. An emulsion according to claim 3, wherein said emulsion is stable as an emulsion after heating to about 49° C. for one week.

6. An emulsion according to claim 3, wherein said emulsion is stable as an emulsion after heating to about 60° C. for twelve hours.

7. An emulsion according to claim 3, wherein said emulsion is stable as an emulsion after heating to about 60° C. for one week.

8. An emulsion according to claim 1, wherein said emulsion is essentially anhydrous.

9. A cosmetic composition comprising
   (i) a stabilized glycerin-in-oil emulsion comprising:
      (a) a continuous phase comprising one or more topically-acceptable oils,
      (b) a discontinuous phase comprising glycerin as the major component, and
      (c) a combination of trihydroxystearin and 12-hydroxystearic acid in an amount suitable to provide a viscosity for the emulsion at room temperature between about 2000 centipoise and about 3 million centipoise, wherein a weight ratio of trihydroxystearin to 12-hydroxystearic acid is not greater than about 5/1; and
   (ii) optionally one or more components distributed in either or both phases of said emulsion, said components selected from the group consisting of pigments, waxes, emollients, moisturizers, preservatives, flavorants, antioxidants, botanicals, and mixtures thereof;
   wherein said emulsion has improved stability compared to an otherwise identical emulsion not containing trihydroxystearin and/or 12-hydroxystearic acid.

10. A cosmetic composition according to claim 9, wherein said cosmetic composition is suitable for application to the lips.

11. A lip product comprising:
(A) a cosmetic composition suitable for application to the lips comprising
    (i) a stabilized glycerin-in-oil emulsion comprising:
        (a) a continuous phase comprising one or more topically-acceptable oils,
        (b) a discontinuous phase comprising glycerin as the major component, and
        (c) a combination of trihydroxystearin and 12-hydroxystearic acid in an amount suitable to provide a viscosity for the emulsion at room temperature between about 2000 centipoise and about 3 million centipoise such that the emulsion has a suitable consistency to be squeezed from a tube, wherein a weight ratio of trihydroxystearin to 12-hydroxystearic acid is not greater than about 5/1; and
    (ii) optionally one or more components distributed in either or both phases of said emulsion, said components selected from the group consisting of pigments, waxes, emollients, moisturizers, preservatives, flavorants, antioxidants, botanicals, and mixtures thereof;
wherein said emulsion has improved stability compared to an otherwise identical emulsion not containing trihydroxystearin and/or 12-hydroxystearic acid; and
(B) a re-closeable container having a chamber at least partially charged with said cosmetic composition and a cap reversibly attached to said container for sealing the contents of the chamber when in a closed position and for permitting said contents to be dispensed when in an open position.

12. A lip product according to claim 11, wherein
(i) said one or more topically-acceptable oils are present in a range from about 40% to about 90% by weight of said cosmetic composition,
(ii) said glycerin is present in a range from about 5% to about 60% by weight of said cosmetic composition,
(iii) said trihydroxystearin is present in a range from about 0.5% to about 2.5% by weight of said cosmetic composition, and
(iv) said 12-hydroxystearic acid is present in a range from about 0.2% to about 1.5% by weight of said cosmetic composition;
wherein said cosmetic composition further comprises:
(v) one or more emulsifiers in a total range from about 0.5 to about 6.0% by weight of said cosmetic composition.

13. A lip product according to claim 11, wherein said lip product is selected from the group consisting of lip cream, lip balm, lip gloss, medicated lip treatment, lip moisturizer, lip cosmetic, lip sunscreen, and lip flavorant.

14. A stabilized glycerin-in-oil emulsion comprising:
(i) a continuous phase comprising one or more topically-acceptable oils; and
(ii) a discontinuous phase comprising glycerin as the major component;
wherein the emulsion exhibits an elastic modulus $(G') \geqq 0$ that is essentially temperature independent at temperatures between about 25° C. to about 60° C.; and
wherein the emulsion comprises a weight ratio of trihydroxystearin to 12-hydroxystearic acid that is not greater than about 5/1.

15. An emulsion according to claim 14, wherein the emulsion exhibits an elastic modulus (G') that is essentially temperature independent at temperatures between about 20° C. to about 80° C.

* * * * *